(12) United States Patent
Sankai et al.

(10) Patent No.: US 10,702,442 B2
(45) Date of Patent: Jul. 7, 2020

(54) WALKING AID DEVICE

(71) Applicants: CYBERDYNE Inc., Tsukuba-shi, Ibaraki (JP); University of Tsukuba, Tsukuba-shi, Ibaraki (JP)

(72) Inventors: Yoshiyuki Sankai, Tsukuba (JP); Masahiro Takama, Tsukuba (JP); Tomoyoshi Kawabata, Tsukuba (JP); Hiromasa Hara, Tsukuba (JP); Ryotaro Sabe, Tsukuba (JP); Martin Peris Martorell, Tsukuba (JP)

(73) Assignees: CYBERDYNE INC., Tsukuba-Shi, Ibaraki (JP); UNIVERSITY OF TSUKUBA, Tsukuba-Shi, Ibaraki (JP)

( * ) Notice: Subject to any disclaimer, the term of this patent is extended or adjusted under 35 U.S.C. 154(b) by 79 days.

(21) Appl. No.: 15/575,266

(22) PCT Filed: May 19, 2016

(86) PCT No.: PCT/JP2016/064939
§ 371 (c)(1),
(2) Date: Nov. 17, 2017

(87) PCT Pub. No.: WO2016/186182
PCT Pub. Date: Nov. 24, 2016

(65) Prior Publication Data
US 2018/0140496 A1    May 24, 2018

(30) Foreign Application Priority Data
May 19, 2015    (JP) .................................. 2015-102221

(51) Int. Cl.
*A61H 3/00*    (2006.01)
*A61B 5/11*    (2006.01)

(52) U.S. Cl.
CPC .............. *A61H 3/008* (2013.01); *A61B 5/112* (2013.01); *A61H 3/00* (2013.01); *A61H 2201/12* (2013.01);
(Continued)

(58) Field of Classification Search
CPC .................... A61H 3/008; A61B 5/112; A63B 22/02–0292
See application file for complete search history.

(56) References Cited

U.S. PATENT DOCUMENTS 7,125,388 B1 * 10/2006 Reinkensmeyer .......................... A63B 69/0064
601/5
9,616,278 B2 * 4/2017 Olson ................ A63B 22/0023
(Continued)

FOREIGN PATENT DOCUMENTS

| JP | S46-013443 Y | 5/1971 |
| JP | H07-236669 A | 9/1995 |

(Continued)

OTHER PUBLICATIONS

International Search Report and Written Opinion for Japanese Patent Application PCT/JP2016/064939, dated Jun. 21, 2016. English translation provided for search report.
(Continued)

*Primary Examiner* — Jennifer Robertson
(74) *Attorney, Agent, or Firm* — Procopio, Cory, Hargreaves & Savitch LLP

(57) ABSTRACT

Provided is a walking aid device capable of easily offering walking training by aiding the oscillation of the user's pelvis. The walking aid device comprises a drive part which supports each of at least two or more locations of the user's lumbar region, and applies external force independently to each of the supported locations; a gait recognition unit
(Continued)

which recognizes the user's gait; and a control unit which sets the user's ideal walking motion pattern based on a recognition result of the gait recognition unit, and controls the external force applied by the drive part to each of the locations of the lumbar region so that the user's pelvis position within the lumbar region will oscillate to match the walking motion pattern.

8 Claims, 14 Drawing Sheets

(52) U.S. Cl.
CPC .............. *A61H 2201/5007* (2013.01); *A61H 2203/0406* (2013.01)

(56) References Cited

U.S. PATENT DOCUMENTS

| | | |
|---|---|---|
| 2010/0076360 A1 | 3/2010 | Shimada et al. |
| 2014/0058299 A1* | 2/2014 | Sankai .................. A61B 5/112 601/35 |
| 2016/0000635 A1 | 1/2016 | Miyake |
| 2017/0027803 A1* | 2/2017 | Agrawal ............. A61B 5/6828 |

FOREIGN PATENT DOCUMENTS

| | | |
|---|---|---|
| JP | H11-113988 A | 4/1999 |
| JP | 2004-201892 A | 7/2004 |
| JP | 2009-183657 A | 8/2009 |
| JP | 2010-75213 A | 4/2010 |
| JP | 2013-183863 A | 9/2013 |
| JP | 2014-128464 A | 7/2014 |
| JP | 2015-62654 A | 4/2015 |
| WO | 2012/118143 A1 | 9/2014 |

OTHER PUBLICATIONS

Notification of Reasons for Refusal for related JP App No. 2017-519405 dated Jun. 4, 2018, 9 pgs.

* cited by examiner (A)  (B)

FIG.7
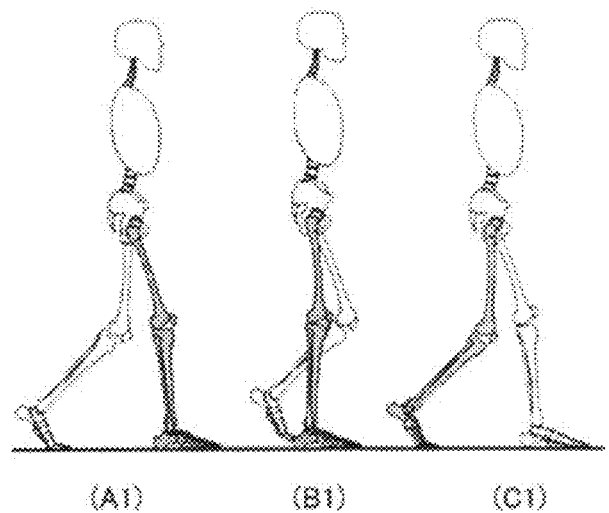
(A1)  (B1)  (C1)
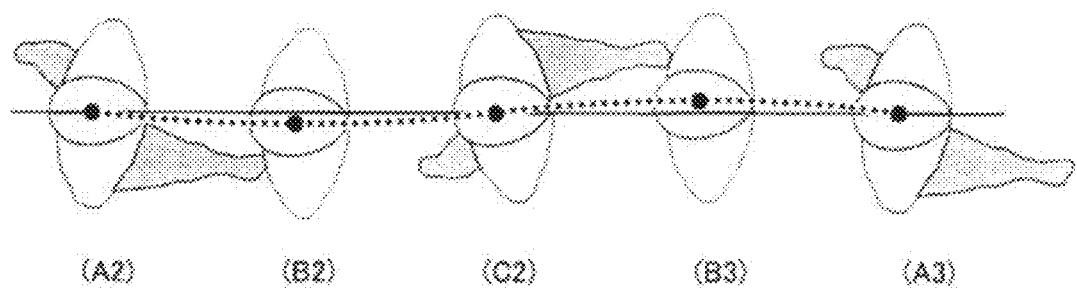
(A2)   (B2)   (C2)   (B3)   (A3)

FIG.8
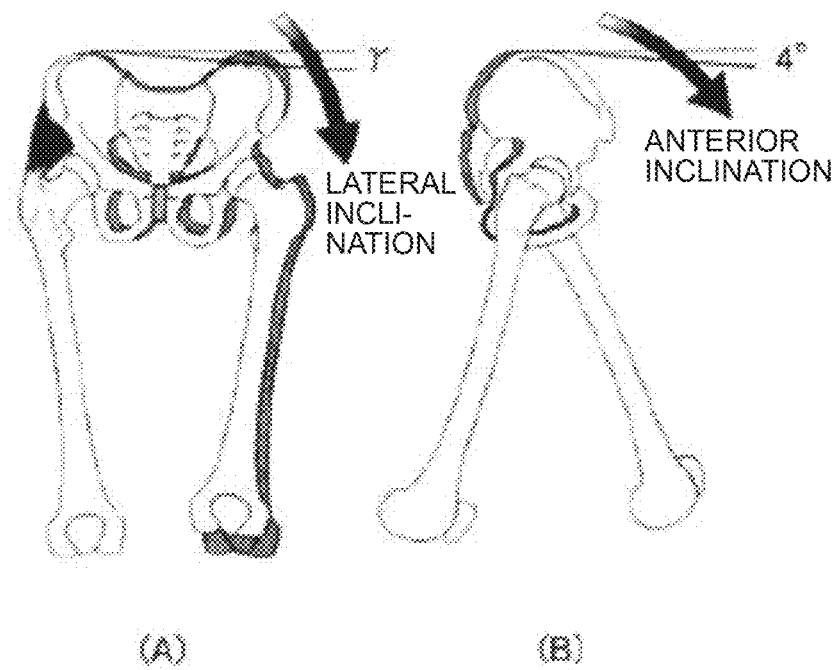
(A)　　　　　　　(B)
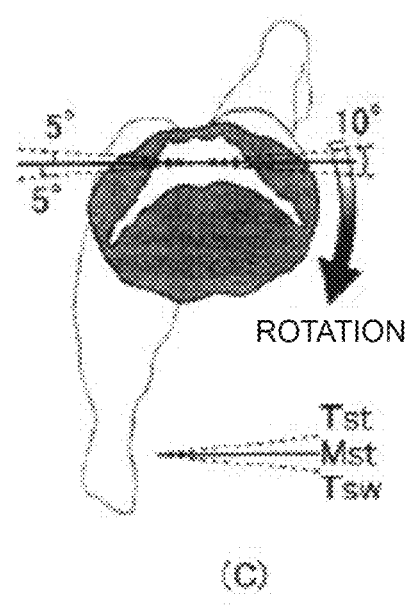
(C)

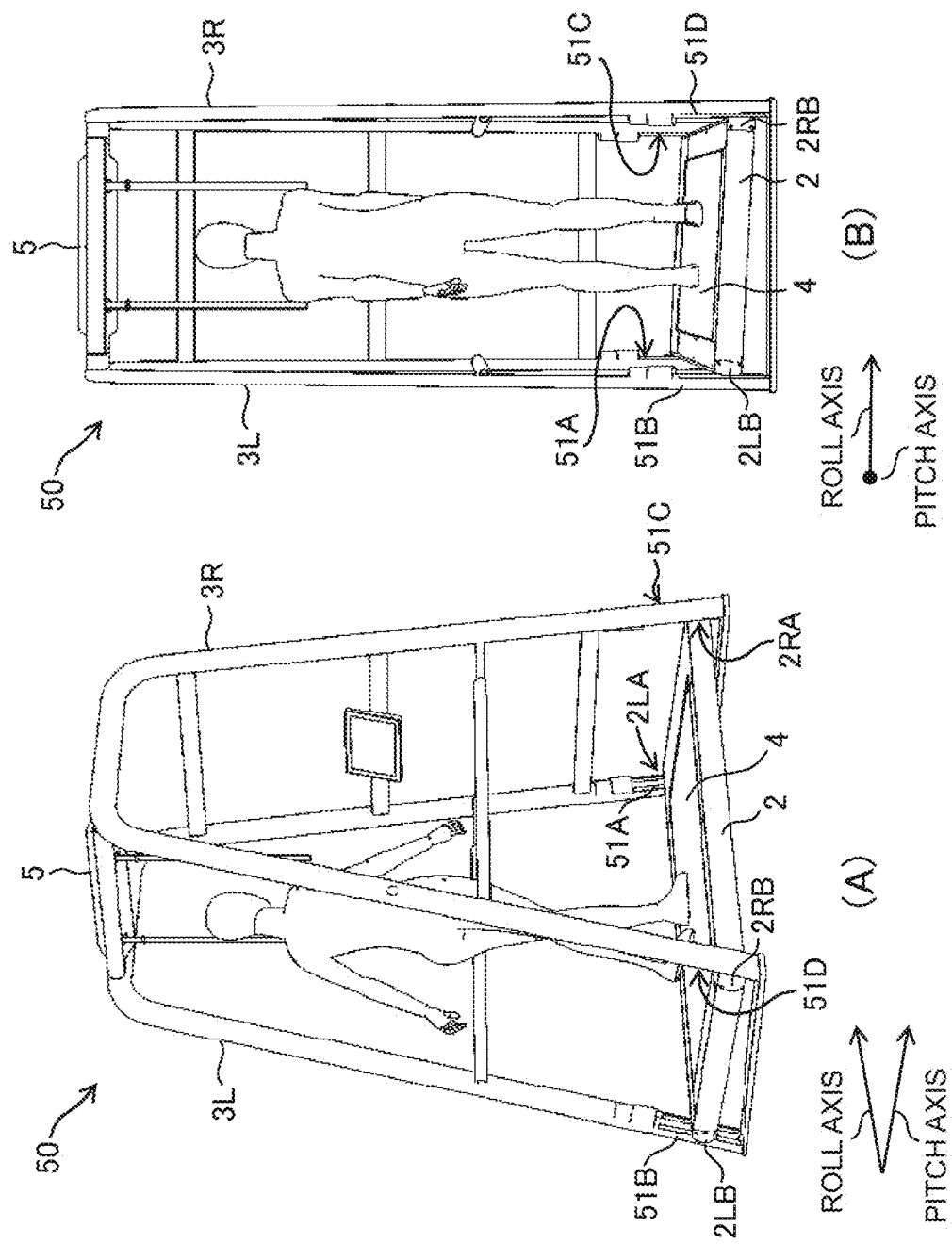

WALKING AID DEVICE

TECHNICAL FIELD

The present invention relates to a walking aid device which aids a user's gait.

BACKGROUND ART

Conventionally, when a person is unable to walk on his/her own due to gait disturbance caused by cerebral paralysis or other reasons, it is known that a rehabilitation effect, such as improvement of ADL (Activities of Daily Living), can be obtained by offering walking training of causing such person to walk on a treadmill in which a walking belt rotates in a circular motion.

For instance, PTL 1 discloses a walking training device in which the subject is lifted with a wire on a force plate having an annular walking surface, and the holding power of the subject's trunk is maintained to be constant by changing the tensile force of the wire according to the excess or deficiency of the surface load of the force plate.

Moreover, also disclosed is a walking aid system in which the trainee is lifted with a relief belt, and the upper body of the trainee is supported and maintained in a normal posture, even when the trainee loses his/her balance, by adjusting the draw-down length of the relief belt according to the change in height of the trainee's waist (refer to PTL 2).

Furthermore, additionally proposed is a nerve rehabilitation device based on walking training of causing a person to walk on a treadmill, wherein the floor reaction is increased/decreased by applying a joint moment to the lower leg joints of the person wearing a walking aid device by controlling the output of the actuator of the walking aid device so as to obtain a floor reaction pattern in which the normal walking pattern of a healthy person is used as the model walking pattern (refer to PTL 3).

CITATION LIST

Patent Literature

[PTL 1] Japanese Patent Application Publication No. H07-236669
[PTL 2] Japanese Patent Application Publication No. 2013-183863
[PTL 3] Japanese Patent Application Publication No. 2010-75213

SUMMARY OF THE INVENTION

Problems to be Solved by the Invention

Nevertheless, with the walking training devices disclosed in PTL 1 and PTL 2 above, because a support belt or the like is wrapped around the user's trunk in order to relieve the load on the user's legs, the oscillation of the user's pelvis, which arises in the walking pattern of a healthy person, becomes inhibited.

Thus, with any walking training that is performed in a state where the user's pelvis is fixed, because the oscillation of the pelvis is inhibited, it becomes difficult for the user to gain the walking ability that is required for walking even after removing the relief.

Meanwhile, even in cases where the user's pelvis is not fixed as with PTL 3 above, with the method of controlling the lifting of the user according to the floor reaction pattern, there is a problem in that the user is unable to naturally learn an ideal walking pattern with ease.

The present invention was devised in view of the foregoing points, and an object of this invention is to provide a walking aid device capable of easily offering walking training by aiding the oscillation of the user's pelvis.

Means to Solve the Problems

The walking aid device according to an embodiment of the present invention comprises a drive part which supports each of at least two or more locations of the user's lumbar region, and applies external force independently to each of the supported locations; a gait recognition unit which recognizes the user's gait; and a control unit which sets the user's ideal walking motion pattern based on a recognition result of the gait recognition unit, and controls the external force applied by the drive part to each of the locations of the lumbar region so that the user's pelvis position within the lumbar region will oscillate to match the walking motion pattern.

ADVANTAGEOUS EFFECTS OF THE INVENTION

According to the present invention, it is possible to realize a walking aid device capable of facilitating walking training by aiding the oscillation of the user's pelvis.

BRIEF DESCRIPTION OF DRAWINGS

FIG. 7 is a conceptual diagram showing the motion of the user's pelvis during a walking motion.
FIG. 8 is a conceptual diagram showing the motion of the user's pelvis during a walking motion.
FIG. 14 is a perspective view and a rear view showing an exterior configuration of the walking aid device according to another embodiment.

DESCRIPTION OF EMBODIMENTS

An embodiment to which the walking aid device of the present invention is applied is now explained.

(1) Configuration of Walking Aid Device According to this Embodiment

Figure 1:
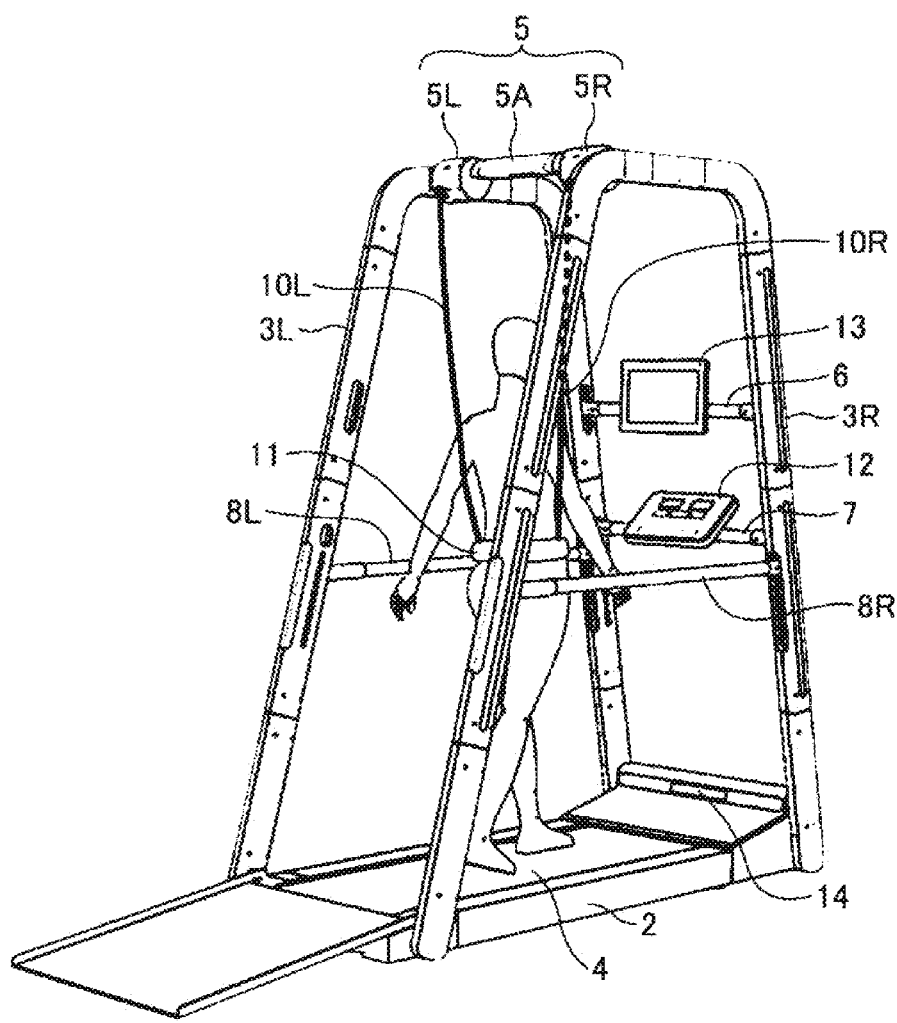
FIG. 1 is a perspective view showing an exterior configuration of the walking aid device according to this embodiment.
Figure 2:
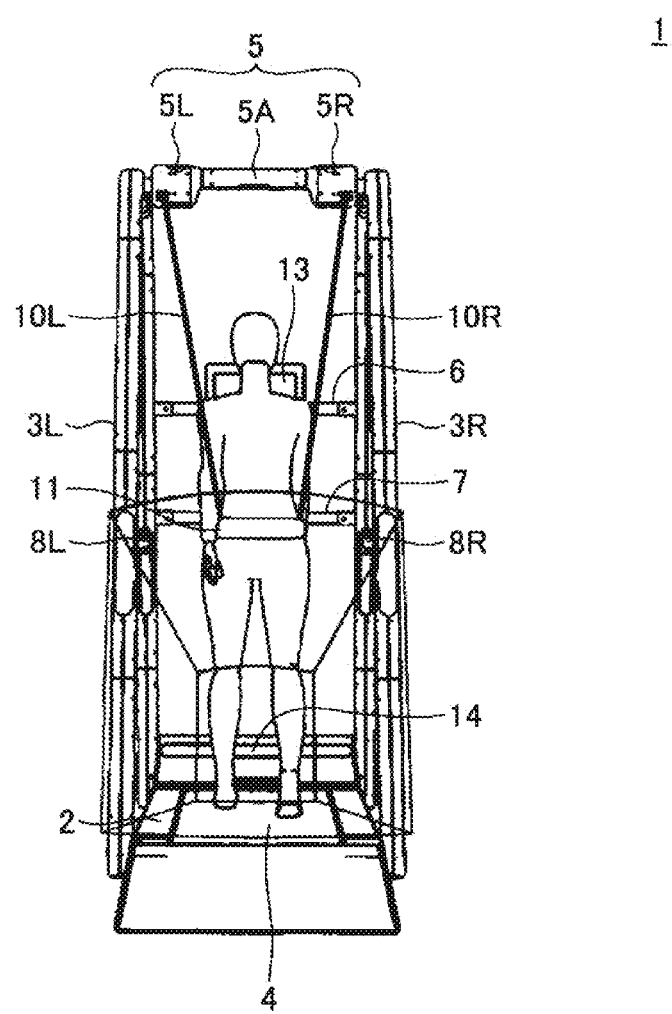
FIG. 2 is a rear view showing an exterior configuration of the walking aid device according to this embodiment.
Figure 3:
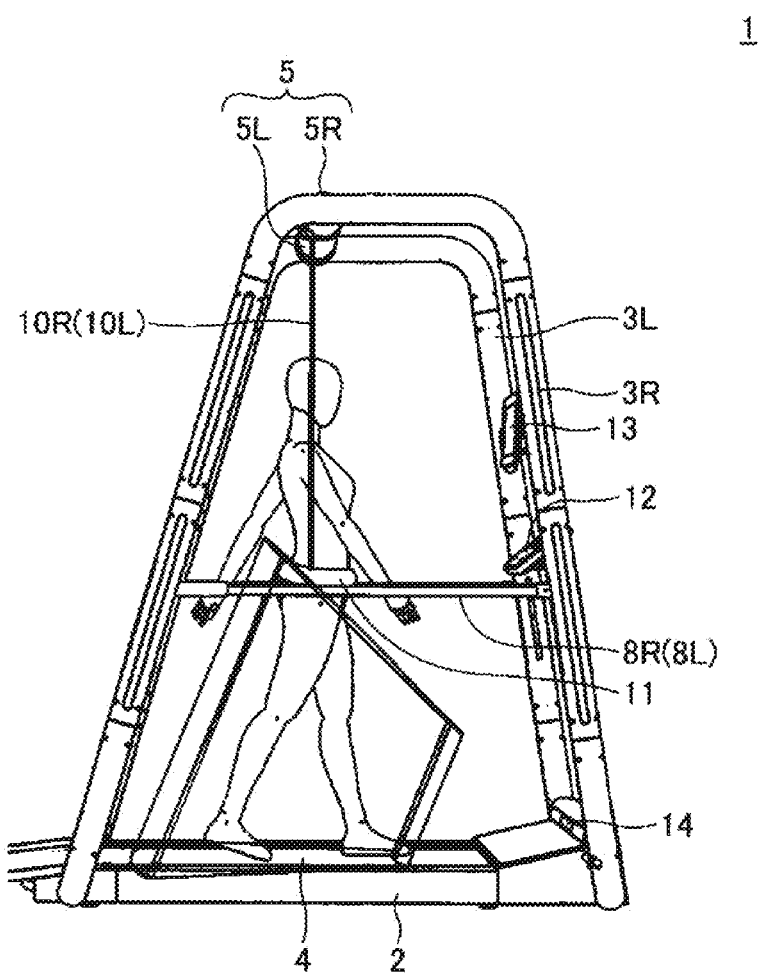
FIG. 3 is a side view showing an exterior configuration of the walking aid device according to this embodiment.

FIG. 1 to FIG. 3 show an exterior configuration of a walking aid device 1 according to this embodiment. In the ensuing explanation, the terms "up/down", "left/right" and "front/rear" are defined based on the user in a state where the user is using the walking aid device 1 as shown in FIG. 1 to FIG. 3. Thus, FIG. 1 is a perspective view showing a state seen from a right oblique rear direction, FIG. 2 is a rear view seen from the rear side, and FIG. 3 is a side view seen from the right side.

The walking aid device 1 configures a frame body in which a left frame 3L and a right frame 3R which form a paired relation on either side of a treadmill 2 are erected from the four corners of the treadmill 2, and which surround the user, from all directions, who is walking on the treadmill 2 between both frames 3L, 3R.

The treadmill 2 has a walking belt 4 which moves in a circular motion based on a rotation of rollers. The circulating speed of the walking belt 4 can be changed by changing the driving speed of the rollers according to the motor drive.

The left frame 3L and the right frame 3R both have a frame body shape similar to an upside down U-shape, and are configured to be symmetrical. As one example, the height of the upper part of the left frame 3L and the right frame 3R is set based on the treadmill 2 so that it will be higher than the height of users of various physical sizes.

A biaxial drive device (drive part) 5 is bridged and fixed between the upper parts of the left frame 3L and the right frame 3R, and two sub frames 6, 7 positioned in front of the user are fixed in a horizontal direction so as to extend across the left frame 3L and the right frame 3R. Furthermore, handrails 8L, 8R are respectively fixed to the left frame 3L and the right frame 3R at a height position corresponding to the user's lumbar region in a state of extending across the front/rear direction.

The biaxial drive device 5 is a biaxial actuator mounted with winding parts (first tension adjusting part and second tension adjusting part) 5L, 5R having a drive motor in which each of a pair of coaxial rotating axes is used as the output axis, and which coaxially connects the winding parts 5L, 5R. Furthermore, a shaft-shaped cylindrical part 5A having a substantially semicircular cross section with a built-in control board (not shown) is integrally connected with both winding parts 5L, 5R in a rod shape and thereby modularized.

One end of the wires (first wire and second wire) 10L, 10R is fixed to each of the pair of winding parts 5L, 5R configuring the biaxial drive unit 5, and the tension of the wires 10L, 10R is adjusted by winding or unwinding each of the wires 10L, 10R. The other end of the wires 10L, 10R is each fixed to the left and right ends of a wearable harness 11 to be attached to the user's lumbar region.

Of the pair of winding parts 5L, 5R configuring the biaxial drive unit 5, one end of the wire 10L, in which the other end is fixed to a location corresponding to the left side of the wearable harness 11, is connected to the left side winding part (first tension adjusting part) 5L, and the left side winding part (first tension adjusting part) 5L adjusts the tension of the wire 10L by winding or unwinding the wire 10L. Moreover, one end of the wire 10R, in which the other end is fixed to a location corresponding to the right side of the wearable harness 11, is connected to the right side winding part (second tension adjusting part) 5R, and the right side winding part (second tension adjusting part) 5R adjusts the tension of the wire 10R by winding or unwinding the wire 10R.

Furthermore, the sub frame 7 which bridges the left frame 3L and the right frame 3R is equipped with an operation unit 12 having an operation panel for inputting the setting of all measurement function systems and drive systems of the walking aid device 1. The user can use the operation unit 12 and adjust the tension of the respective wires 10L, 10R by the left and right winding parts 5L, 5R of the biaxial drive device 5 and adjust the speed of the walking belt 4 of the treadmill 2.

Furthermore, the sub frame 6 which bridges the left frame 3L and the right frame 3R is equipped with a monitor 13 configured from a liquid crystal display or the like which is able to display the operation result of the operation unit 12 and various types of information required for the user's walking aid.

A motion recognition sensor (gait recognition unit) 14 configured from a RGB-D sensor or the like is mounted between the front side support columns of the left frame 3L and the right frame 3R at the front of the treadmill 2 (walking direction viewed from the user). The motion recognition sensor 14 is configured from a depth sensor capable of measuring the distance to the object seen from the camera in addition to a RGB color camera function, and captures the subject in a state where a single pattern of structured light is projected on the subject, and thereby calculates the depth of the respective points on the image based on triangulation by using the parameters thereof.

For example, as the motion recognition sensor 14, for instance, when Kinect (Microsoft Corporation, registered trademark) is applied as the RGB-D sensor, it is possible to capture the following range; specifically, horizontal visual field of 57 degrees, vertical visual field of 43 degrees, and sensor range of 1.2 m to 3.5 m, and the RGB image can be acquired in 640×480 pixels and the depth image can be acquired in 320×240 pixels at 30 frames/second.

Note that the motion recognition sensor 14 is set so that its height from the floor surface is positioned to be higher than the walking belt 4 of the treadmill 2 by several centimeters to several ten centimeters. The motion recognition sensor 14 is thereby able to three-dimensionally scan the movement of the user's left lower extremity and right lower extremity, and recognize the user's gait (walking posture and movement form of both lower extremities).

(2) User's State of Wearing Wearable Harness

Figure 4:
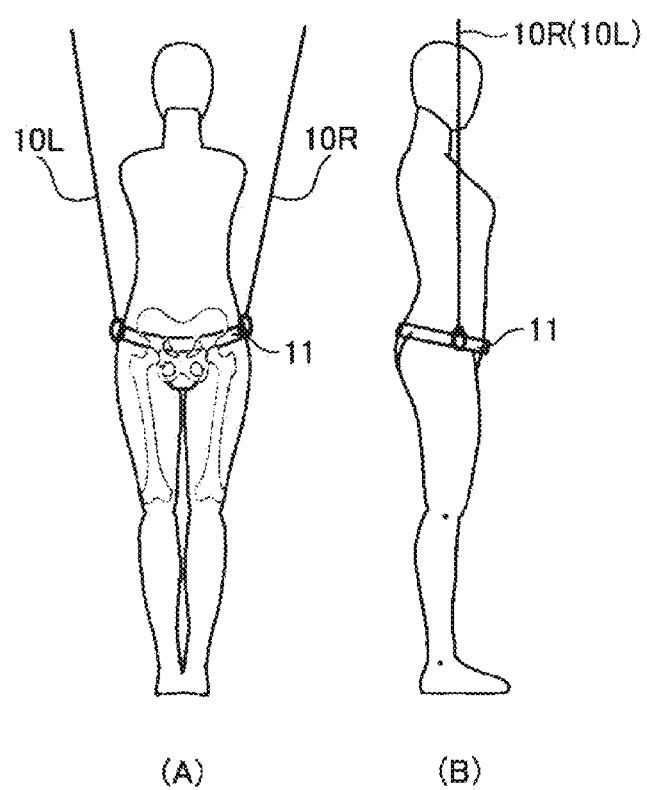
FIG. 4 is a schematic diagram showing a state where the user is wearing the wearable belt of the walking aid device according to this embodiment.

As shown in FIG. 4(A) and FIG. 4(B), the wearable harness 11 is attached around the circumference of the user's lumbar region. Here, the wearable harness 11 supports the user's lumbar region, and is simultaneously wound at a tightness level so that it becomes integrated with the pelvis within the lumbar region.

While it is most desirable to attach the wearable harness 11 to the lumbar region in order to oscillate the user's pelvis, the wearable harness 11 may also be attached to a location other than the lumbar region such as the user's trunk or shoulders so as long as it is possible to oscillate the user's pelvis.

One end of the wire 10L, in which the other end is connected to the winding part 5L, is connected to a location corresponding to the left side of the lumbar region of the wearable harness 11, and one end of the wire 10R, in which the other end is connected to the winding part 5R, is connected to a location corresponding to the right side of the lumbar region of the wearable harness 11.

Consequently, even when the level of increase/decrease of the tension of the respective wires 10L, 10R is changed as a result of the left and right winding parts 5L, 5R of the biaxial drive device 5 winding or unwinding the wires 10L, 10R, the user's pelvis can be oscillated via the wearable harness 11.

Figure 5:
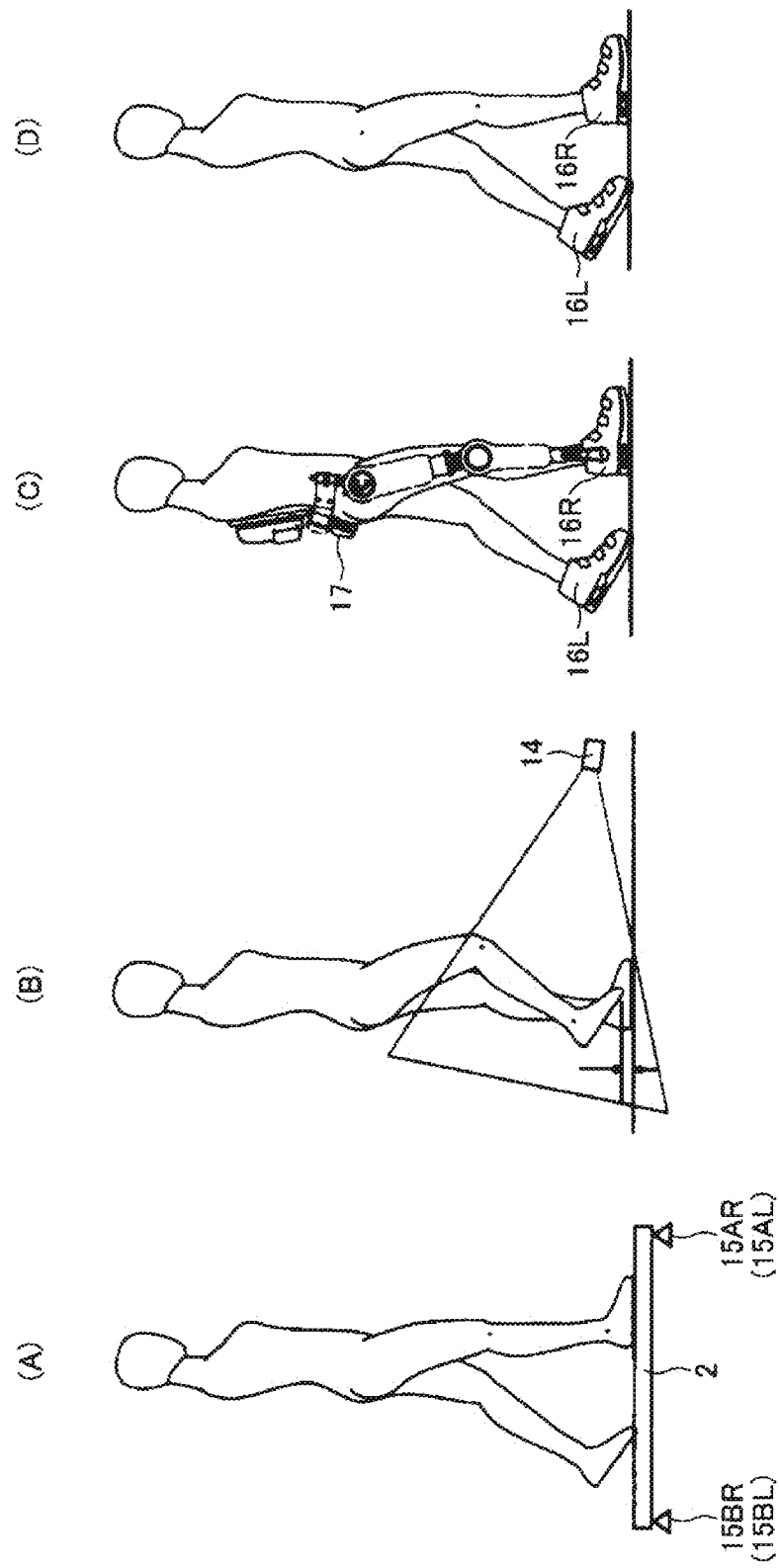
FIG. 5 is a conceptual diagram showing various types of modes of the motion recognition sensor.

While this embodiment explained a case of applying a RGB-D camera as the motion recognition sensor 14 and three-dimensionally scanning the movement of the left lower extremity and the right lower extremity of the user walking on the walking belt 4 of the treadmill 2 and thereby recognizing the user's gait (walking posture and movement form of both lower extremities) (FIG. 5(B)), the present invention is not limited thereto, and various measurement units (not shown) for measuring the centroid position as shown in FIG. 5(A), FIG. 5(C) and FIG. 5(D) may be applied to detect the user's centroid position, and thereby recognize the user's walking state in real time based on the detection result.

For instance, as shown in FIG. 5(A), a plurality of load sensors (force detection sensors such as strain gauges) 15AL, 15AR, 15BL, 15BR including at least four corners may be provided within the treadmill 2, and the centroid position corresponding to the walking motion of the user walking on the walking belt 4 may be obtained based on the change in the load detected by the respective load sensors 15AL, 15AR, 15BL, 15BR.

Furthermore, as shown in FIG. 5(D), special shoes 16L, 16R having a centroid sensor (reaction sensor such as a pressure-sensitive sensor) and a position sensor may be worn on the left and right feet to obtain the centroid position corresponding to the user's walking motion. The centroid position is obtained from the change in the load of both the left and right feet by detecting the load applied to the sole of both the left and right feet pursuant to the user's walking motion.

Moreover, as shown in FIG. 5(C), the user may wear a body-worn motion aid device 17 which aids the motion of the user's leg joints, and a part of the function of the body-worn motion aid device 17 (floor reaction detection function) may be used to detect the user's centroid position. The body-worn motion aid device 17 is a device which generates power according to the user's intention by using biological signals resulting from the walking motion, classifies the user's respective motion patterns as tasks configured from a series of phases (minimum motion unit), estimates the phase of the user's task by using physical quantities such as the rotating angle of the user's leg joints and the floor reaction, and generates power according to the estimated phase. Similar to the special shoes described above with reference to FIG. 5(D), the shoes 16L, 16R of the body-worn motion aid device are also equipped with a centroid sensor and a position sensor.

Figure 6:
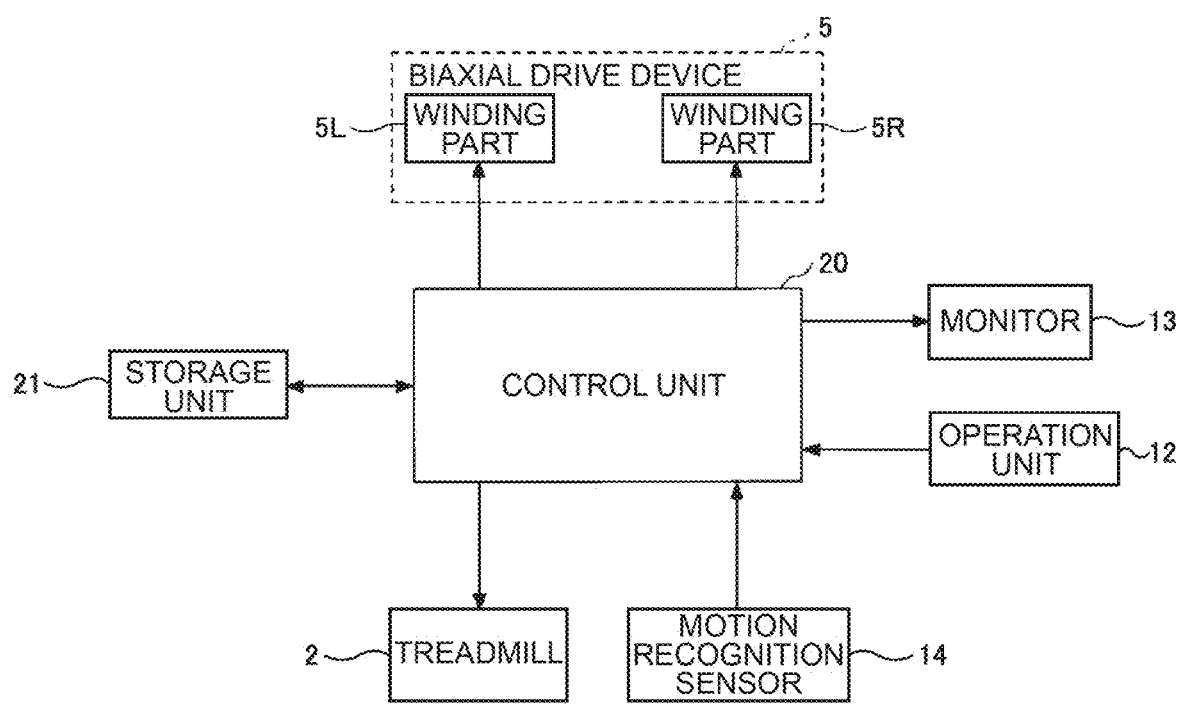
FIG. 6 is a block diagram showing a configuration of the control system of the walking aid device.

(3) Configuration of Control System of Walking Aid Device According to this Embodiment FIG. 6 shows a block diagram indicating the configuration of the control system of the walking aid device 1 according to this embodiment. The walking aid device 1 includes a control unit 20 which governs the control of the overall device, and a computer unit including a CPU (Central Processing Unit) core and a memory may be used as the control unit 20.

When the control unit 20 receives a detection signal from the motion recognition sensor 14 which recognizes the user's gait, the control unit 20 sets the user's ideal walking motion pattern.

Specifically, the control unit 20 measures the stride, walking cycle and walking speed during the user's walking motion based on the detection signal from the motion recognition sensor 14, and thereafter generates pattern data of the ideal walking motion pattern by setting, based on the measurement result, each of the user's pelvis inclination and rotation angle and speed thereof as optimal values of the ideal walking motion pattern with the user's supported state as a reference.

Subsequently, the control unit 20 stores the pattern data representing the ideal walking motion pattern in the storage unit 21, and additionally reads the pattern data as needed. The storage unit 21 registers and stores the optimal pattern data for each of a plurality of users, and, when the user is designated by using the operation unit 12 and the monitor 13, the control unit 20 reads the pattern data corresponding to the designated user.

The control unit 20 controls the left and right winding parts 5L, 5R configuring the biaxial drive device 5 based on the ideal walking motion pattern and adjusts the winding rate or unwinding rate of the wires 10L, 10R drawn out from the respective winding parts 5L, 5R, and thereby adjusts the level of increase/decrease of the tension of the respective wires 10L, 10R.

Consequently, the control unit 20 can oscillate the user's pelvis position within the lumbar region via the locations where the left and right wires of the wearable harness 11 are fixed in synchronization with the ideal walking motion pattern.

Moreover, the control unit 20 oscillates the user's pelvis position within the lumbar region in real time based on the recognition result of the user's gait by the motion recognition sensor 14, and simultaneously controls the speed of the walking belt 4 of the treadmill 2 to match the user's walking speed.

(4) Oscillating State of User's Pelvis Position

The movement of the user's pelvis within the lumbar region pursuant to the user's walking motion is now explained with reference to FIG. 7 and FIG. 8. In the walking aid device 1, the control unit 20 (FIG. 6) sets the ideal walking motion pattern based on the recognition result of the user's gait.

The ideal walking motion pattern is set by three-dimensionally scanning the gait condition which matches the user's actual walking motion. Specifically, the stride, walking cycle and walking speed during the user's walking motion are measured, and, based on the measurement result, each of the user's pelvis inclination and rotation angle and speed thereof are set as optimal values (values in which the time-oriented trunk balance is optimal) of the ideal walking motion pattern with the user's supported state by the wearable harness 11 as a reference.

In effect, with regard to the user's lumbar region, the overall pelvis swings alternately from side to side based on the walking direction to match changes in the time-orientated centroid position of the left leg and the right leg pursuant to the user's walking motion, and the pelvis itself engages in three-dimensional inclination oscillation and rotation oscillation based on the user's trunk.

For example, FIG. 7(A1), (B1), (C1) show the movement of the right leg in the user's walking motion (stance phase in a state where the right leg is touching the ground), and FIG. 7(A2), (B2), (C2), (B3), (A3) show the changes in the centroid position associated with such movement of the right leg.

At the start point of the swing phase in the walking motion where the left leg is off the ground (FIG. 7(A1)), while the weight starts to become applied to the right leg and the centroid position coincides with the walking direction (FIG. 7(A2)), at the center point of the swing phase where the left leg is off the ground (FIG. 7(B1)), the entire weight is applied to the right leg and the centroid position swings to the right side relative to the walking direction (FIG. 7(B2)).

Subsequently, at the point that the stance phase of the right leg is ended and the swing phase is started (FIG. 7(C1)), while the weight starts to become applied to the left leg and the centroid position coincides with the walking direction (FIG. 7(C2)), at the center point of the swing phase of the right leg, the entire weight is applied only to the left leg and the centroid position swings to the left side relative to the walking direction (FIG. 7(B3)). Similarly, at the point that the stance phase of the left leg is ended and the swing phase is started (FIG. 7(A1)), the weight starts to become applied to the right leg and the centroid position coincides with the walking direction (FIG. 7(A3)). Thereafter, the time-oriented centroid position swings alternately from side to side relative to the walking direction pursuant to the walking motion.

Moreover, as shown in FIG. 8(A) to FIG. 8(C), the user's pelvis itself within the lumbar region oscillates three-dimensionally based on the user's trunk. In other words, the user's pelvis inclines alternately from side to side at a predetermined angle (for instance, 7 degrees) based on the user's trunk pursuant to the user's walking motion (FIG. 8(A)), inclines forward at a predetermined angle (for instance, 4 degrees) based on the user's trunk (FIG. 8(B)), and additionally rotates alternately from side to side at a predetermined angle (for instance, 5 degrees) based on the user's trunk (FIG. 8(C)).

(5) Other Embodiments

Figure 9:
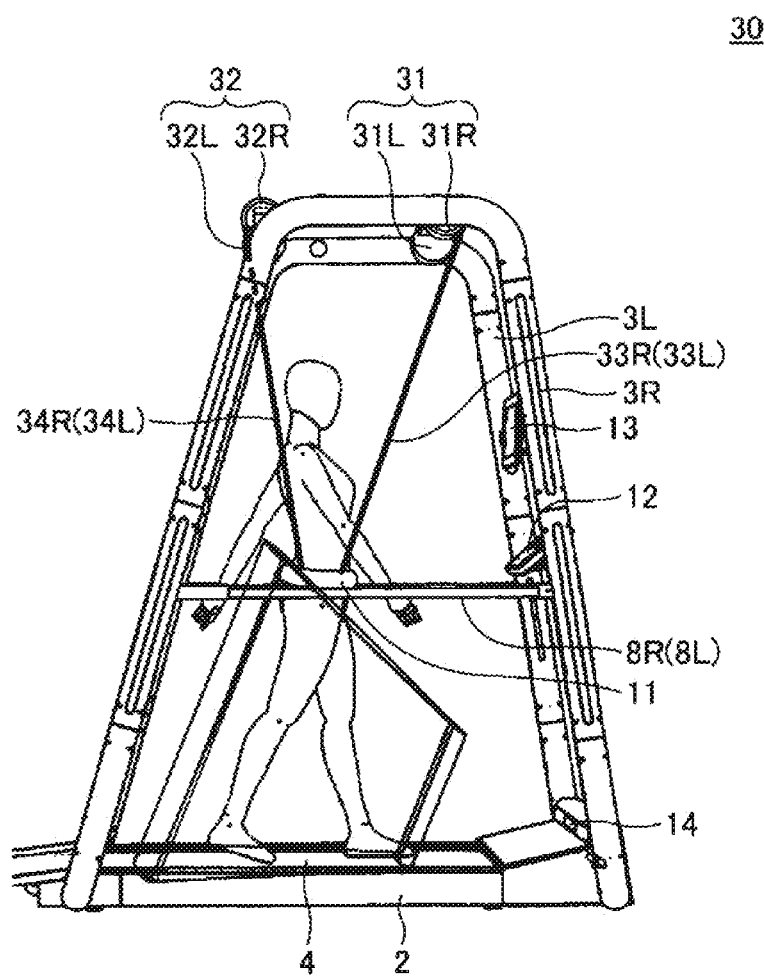
FIG. 9 is a side view showing an exterior configuration of the walking aid device according to another embodiment.

While this embodiment explained a case of fixing the biaxial drive device 5 as a drive part having a pair of left and right winding parts 5L, 5R only at one location at the respective upper parts of the left frame 3L and the right frame 3R, the present invention is not limited thereto, and, as with the walking aid device 30 shown in FIG. 9, two biaxial drive devices 31, 32 may be fixed so as to bridge the respective front upper parts and the respective rear upper parts of the left frame 3L and the right frame 3R based on the user's support position.

When the two biaxial drive devices 31, 32 are to be used as the drive parts, left side winding parts 31L, 32L and right side winding part 31R, 32R may be assigned for support to each of the two locations which form a mutually right-and-left paid relation on the front side and the rear side of the walking direction based on the user's lumbar region in the wearable harness 11 to be attached to the user's lumbar region.

In the foregoing case, because corresponding winding parts are connected, via the wires 33L, 33R, 34L, 34R, from the left and right front side and rear side locations of the wearable harness 11 to be attached to the user's lumbar region, the user's pelvis can be oscillated three-dimensionally by the two biaxial drive devices 31, 32 in the respective directions of upper left forward direction, upper right forward direction, upper right rear direction, and upper right front direction based on the user's support position.

Furthermore, if three or more biaxial drive devices 5 (31, 32) are provided and the number of wire fixing locations in the wearable harness 11 is also increased by the same number, the user's pelvis within the lumbar region can be oscillated three-dimensionally in even more directions to further match the ideal walking motion pattern.

Moreover, while this embodiment explained a case where the biaxial drive device 5 is applied to a walking aid device 1 that is fixed to the floor surface based on a frame structure mounted integrally with the treadmill 2, the present invention is not limited thereto, and the walking aid device 1 may also be applied to a walking training device capable of moving together with the user's gait.

Figure 10:
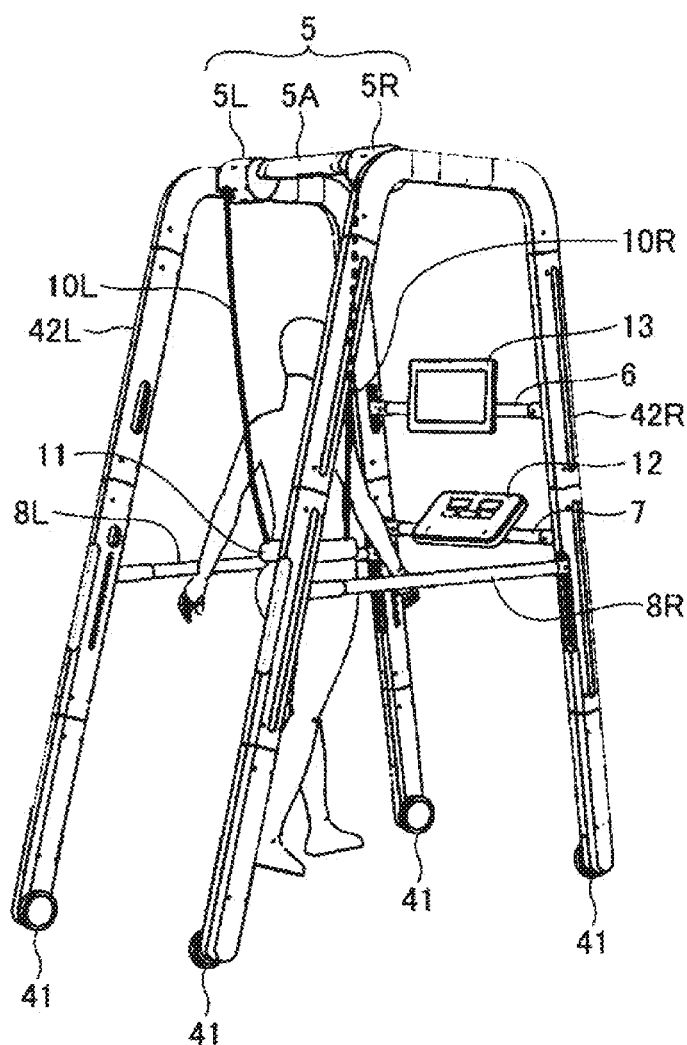
FIG. 10 is a perspective view showing an exterior configuration of the walking aid device according to another embodiment.

FIG. 10 shows a walking aid device 4 as a walking training device according to another embodiment. The walking aid device 40 configures a frame body in which a left frame 42L and a right frame 42R which form a paired left-and-right relation mounted with rotatable wheels 41 at the lower end thereof, and which surrounds the user, and is able to move integrally with the left frame 42L and the right frame 42R.

Unlike the walking aid device 1 shown in FIG. 1, the walking aid device 40 does not have a treadmill, but is configured basically the same other than that it is able to move integrally with the left frame 42L and the right frame 42R. The user wearing the wearable harness 11 is supported by a pair of winding parts 5L, 5R of the biaxial drive device (drive part) 5 bridging the upper parts of the left frame 42L and the right frame 42R in a manner where tension can be adjusted via the wires 10L, 10R.

Accordingly, because the left frame 42L and the right frame 42R move integrally in the same direction pursuant to the user engaging a walking motion of holding the handrails 8L, 8R with both hands and pushing the walking aid device 40 in his/her intended direction, it is possible to offer walking training capable of further improving the user's ADL.

Furthermore, in embodiment, the mobile walking aid device 40 may be provided with auxiliary force based on automatic drive. In other words, a wheel drive part (not shown) capable of independently driving each of the wheels 40 according to the control of the control unit 20 is engaged with at least a pair of left and right wheels 41 among the plurality of wheels 41 mounted at the lower end of the left frame 42L and the right frame 42R, and the control unit 20 controls the wheel drive part so as to adjust the driving speed and the rotating direction of the respective wheels 41 to match the user's walking motion based on a recognition result of a motion recognition sensor (gait recognition unit) not shown in FIG. 10. Consequently, because auxiliary force of the walking motion is automatically applied for users in which normal walking training is difficult, further improvement effects can be expected.

Figure 11:
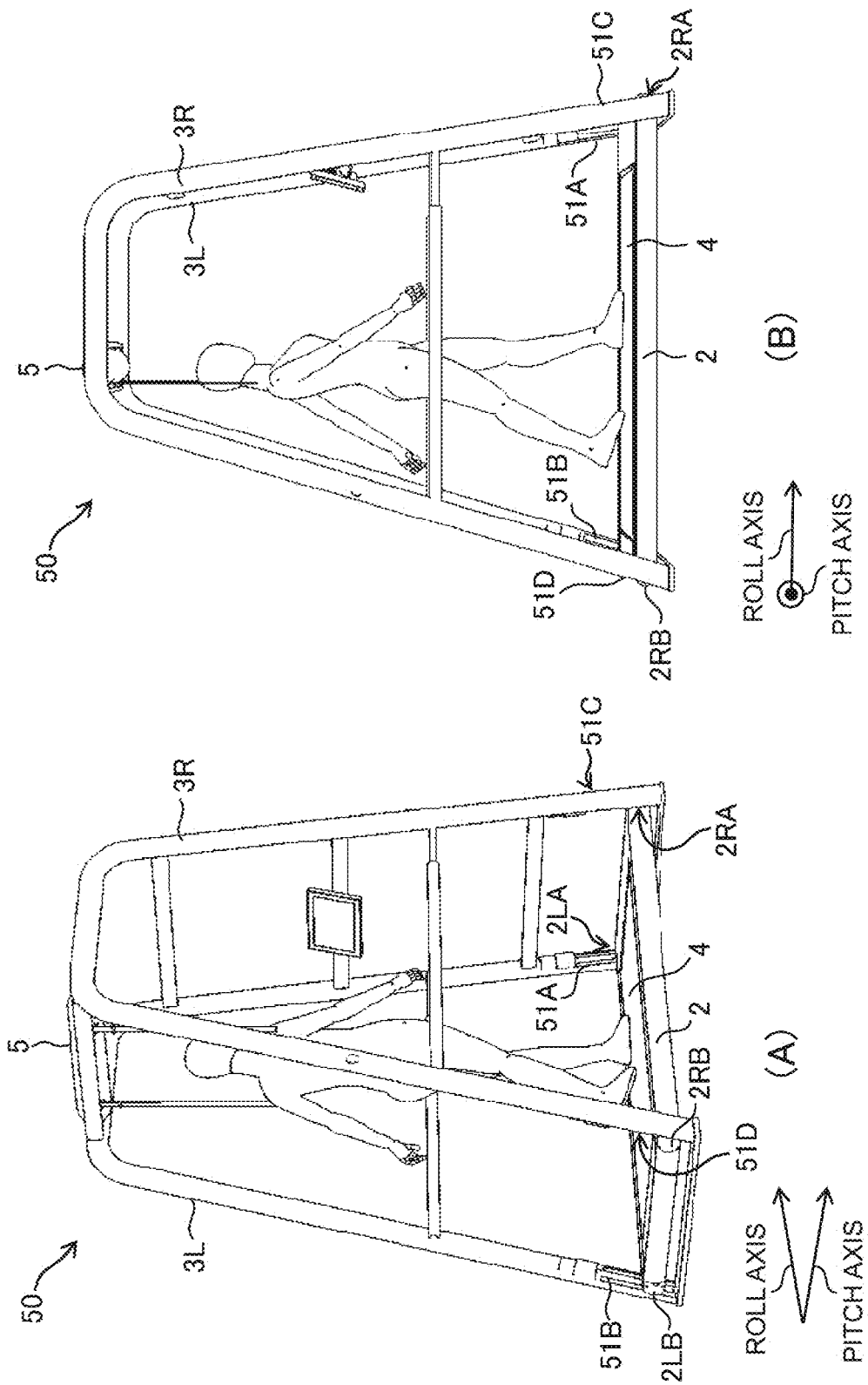
FIG. 11 is a perspective view and a side view showing an exterior configuration of the walking aid device according to another embodiment.
Figure 12:
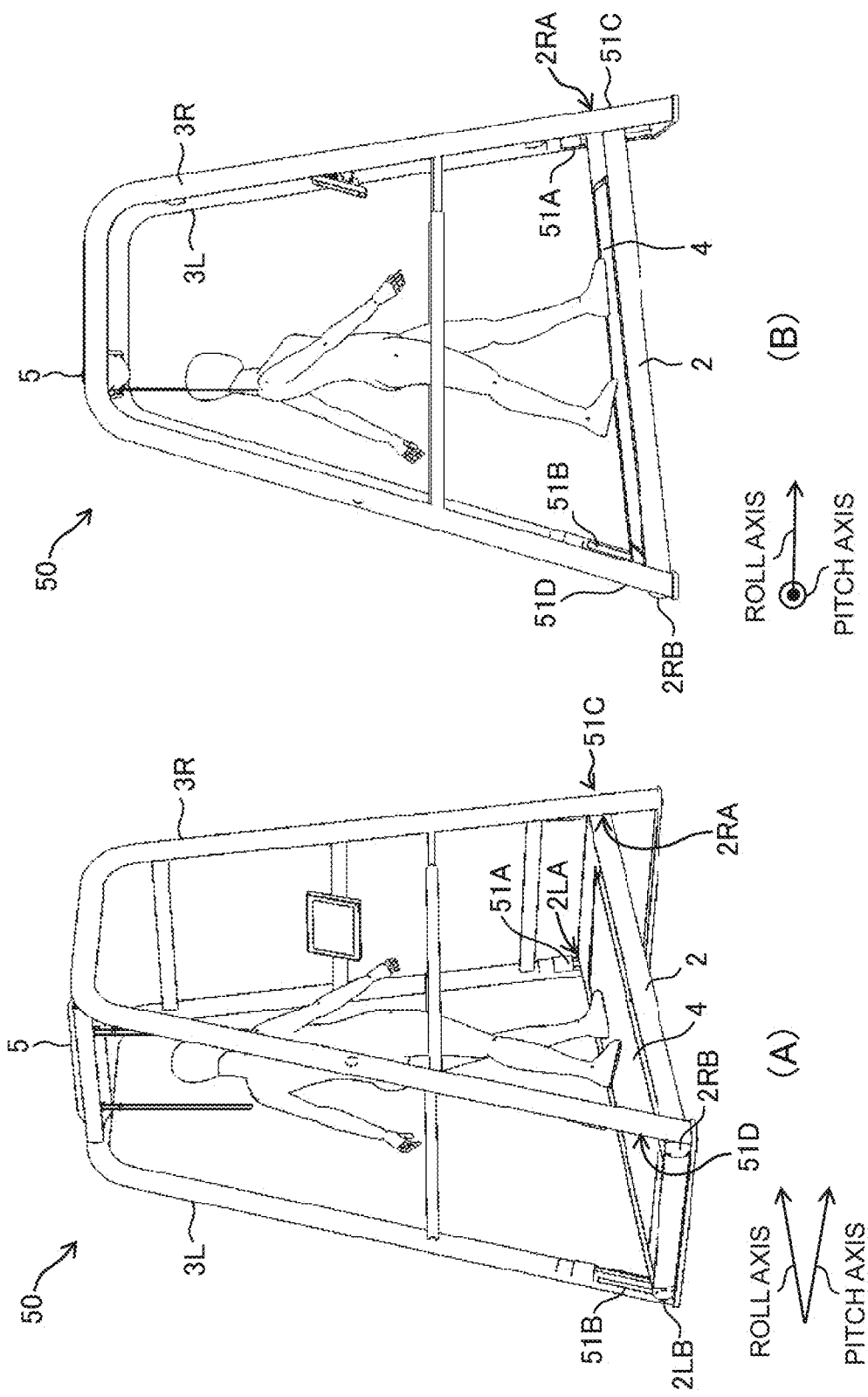
FIG. 12 is a perspective view and a side view showing an exterior configuration of the walking aid device according to another embodiment.
Figure 13:
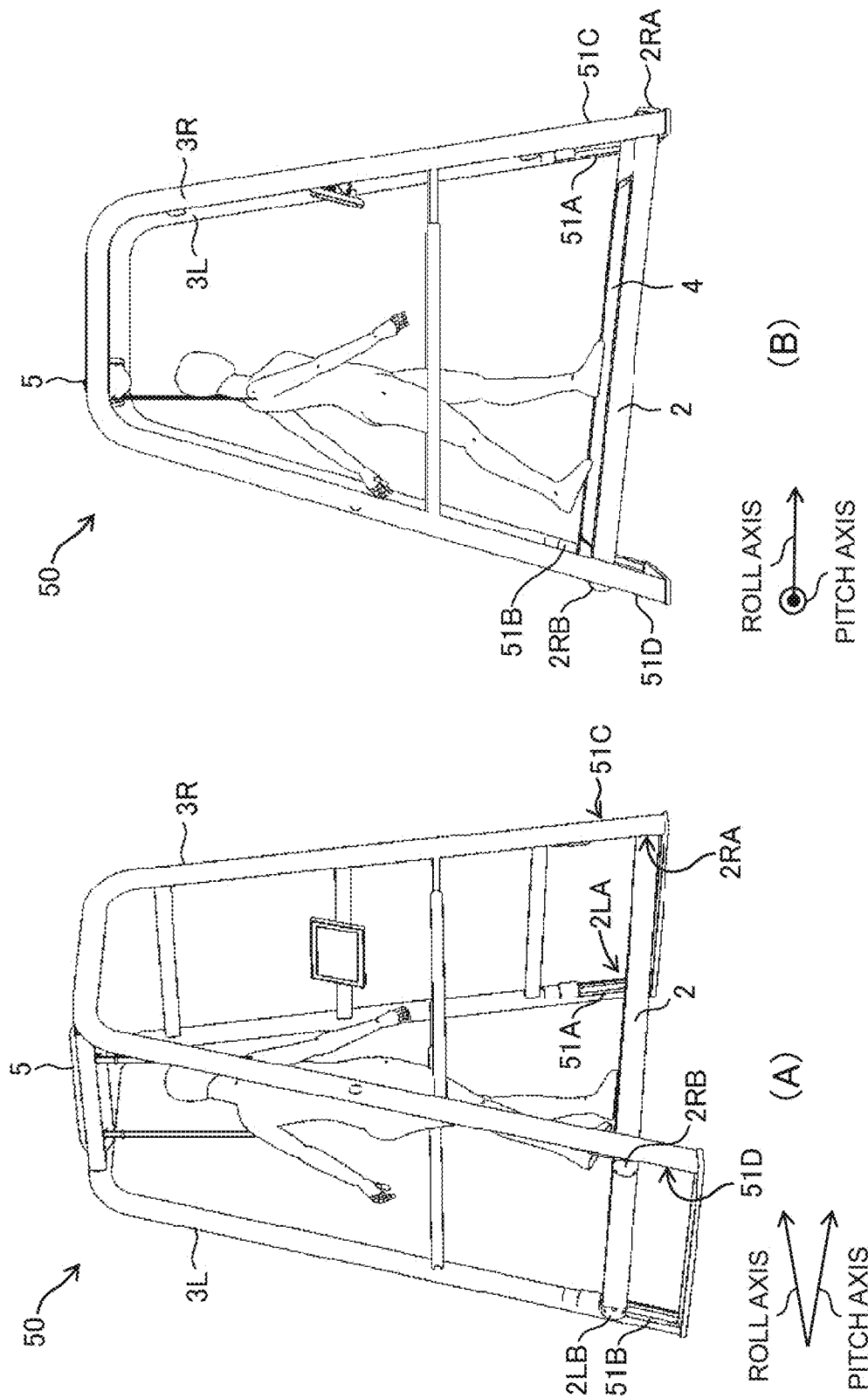
FIG. 13 is a perspective view and a side view showing an exterior configuration of the walking aid device according to another embodiment.

Furthermore, while this embodiment explained a case where the treadmill 2 is placed on a flat floor surface, the present invention is not limited thereto, and, as with the walking aid device 50 shown in FIG. 11(A) and FIG. 11(B), the four corners of the treadmill 2 may be independently supported at the ground end of the frame so that the height can be freely adjusted.

In other words, with the walking aid device 50, adjustment mechanism parts 51 (51A to 51D) are respectively provided near the respective ground ends of the left frame 3L and the right frame 3R, and the four corners (support locations) 2LA, 2LB, 2RA, 2RB of the treadmill 2 are supported in a state where the walking belt 4 can move in a circular motion. The respective adjustment mechanism parts 51A to 51D have an actuator 52 and a ball screw 53 at the support locations 2LA, 2LB, 2RA, 2RB which support the corners of the treadmill 2, and the ball screws 53 lift and move the support locations 2LA, 2LB, 2RA, 2RB while converting rotational motion into linear motion according to the drive of the actuators 52.

With the walking aid device 50, as shown in FIG. 12(A) to FIG. 13(B), among the plurality of support locations 2LA, 2LB, 2RA, 2RB, by respectively adjusting the support locations 2LA, 2RA forming a front side pair relation and the support locations 2LB, 2RB forming a rear side pair relation relative to the advancing direction of the treadmill 2 by predetermined heights, the walking surface of the walking belt is inclined relative to the floor surface at an angle corresponding to the predetermined height around the pitch axis.

Moreover, with the walking aid device 50, as shown in FIG. 14(A) and FIG. 14(B), among the plurality of support locations 2LA, 2LB, 2RA, 2RB, by respectively adjusting the support locations 2LA, 2LB forming a left side pair relation and the support locations 2RA, 2RB forming a right side pair relation relative to the advancing direction of the treadmill 2 by predetermined heights, the walking surface of the walking belt 4 is inclined relative to the floor surface at an angle corresponding to the predetermined height around the roll axis.

When the angle of inclination around the pitch axis or the roll axis on the walking surface of the walking belt 4 is externally input via the operation panel of the operation unit 12, the control unit 20 of the walking aid device 50 drives each of the corresponding actuators so that the respective support locations 2LA, 2LB, 2RA, 2RB are positioned at the height corresponding to the angle of inclination.

As the effects of actually inclining the treadmill 2 in the front, rear, left or right direction in the walking aid device 50, it is possible to build a walking motion pattern that matches the user's symptom and expect a considerable improvement effect in the user's gait.

For example, if the user is a hemiplegic patient, it is often the case that the user suffers from a walking pattern of swinging his/her legs toward the outside with straightened knees as a result of not being able to raise one's pelvis (so-called, circumduction gait). As a result of inclining the treadmill 2 to either the left or the right to match the inclination timing of the walking surface of the walking belt 4 based on the lifted leg and the supporting leg during the user's gait, it is possible to enable the user to walk more easily even when the user suffers from a circumduction gait.

Moreover, as a result of inclining the treadmill 2 to either the front or the rear so that the walking surface of the walking belt 4 will form an upward slope or a downward slope relative to the advancing direction during the user's gait, load can be applied to the walking motion in comparison to cases where the walking surface is flat. Consequently, upon measuring the user's physical data during his/her walking motion (for instance, bioelectric potential, centroid position, gait, heart rate, body surface temperature, stride, etc.), the measurement time can be shortened because the considerable improvement effect of the gait can be expected for the amount of load that is applied.

While a case was explained where an actuator and a ball screw were provided as the adjustment measurement parts 51 (51A to 51D) at the support locations of the four corners of the treadmill, various types of mechanisms that convert the actuator's rotational motion into linear motion, such as trapezoidal threads, may also be applied other than the ball screws as the lifting mechanism of lifting and moving the respective support locations according to the drive of the actuator.

REFERENCE SIGNS LIST 1, 30, 40, 50 . . . walking aid device, 2 . . . treadmill, support locations . . . 2LA, 2LB, 2RA, 2RB, 3L, 42L . . . left frame, 3R, 42R . . . right frame, 4 . . . walking belt, 5 . . . biaxial drive device, 5L, 5R . . . winding part, 6, 7 . . . sub frame, 8L, 8R . . . handrail, 10L, 10R, 33L, 33R, 34L, 34R . . . wire, 11 . . . wearable harness, 12 . . . operation unit, 13 . . . monitor, 14 . . . motion recognition sensor, 20 . . . control unit, 21 . . . storage unit, 41 . . . wheels, 51 (51A to 51D) . . . adjustment mechanism parts.

The invention claimed is:
1. A walking aid device which aids a user's gait, comprising:
   a drive part which includes a first tension adjusting part configured to adjust tension of a first wire in which one end is configured to be fixed to a location corresponding to a left side of a user's lumbar region, a second tension adjusting part configured to adjust tension of a second wire in which one end is configured to be fixed to a location corresponding to a right side of the user's lumbar region, and a frame erected relative to a walking surface of a walking belt and supports the first tension adjusting part and the second tension adjusting part so that they are configured to attain a mutually right-and-left paired relation at a position that is higher than the user's lumbar region, and the drive part is configured to apply external force independently via the first wire and the second wire while being configured to support each of the locations corresponding to the left side and the right side of the user's lumbar region;
   a gait recognition unit configured to measure a user's stride, walking cycle, walking speed and centroid position during a user's walking motion and recognizes a user's gait; and
   a control unit configured to set a user's ideal walking motion pattern by setting each of a user's pelvis inclination and rotation angle and speed thereof as optimal values, in which a time-oriented trunk balance is optimal, of the ideal walking motion pattern with a user's supported state as a reference based on a recognition result of the gait recognition unit,
   wherein the control unit is configured to drive the first tension adjusting part and the second tension adjusting part in synchronization with the walking motion pattern to respectively control a level of increase/decrease of tension of the first wire and tension of the second wire such that (i) a user's overall pelvis may swing alternately from side to side based on a walking direction to match changes in a time-orientated centroid position of a user's left leg and right leg and (ii) the user's pelvis itself engages in three-dimensional inclination oscillation and rotation oscillation based on a user's trunk.
2. The walking aid device according to claim 1, further comprising:
   a storage unit configured to store pattern data representing the ideal walking motion pattern which is measured in advance for each of a plurality of users, wherein the control unit is configured to read the pattern data corresponding to a designated user from the storage unit as the recognition result of the gait recognition unit, and thereafter controls the first tension adjusting part and the second tension adjusting part to match the ideal walking motion pattern based on the pattern data read by the control unit.

3. The walking aid device according to claim 1,
wherein the drive part, among each of the locations within the user's the lumbar region, is configured to assign the first tension adjusting part and the second tension adjusting part to each of a predetermined number of locations which attain a mutually paired positional relation on the left side and the right side of the lumbar region and is thereby configured to support the locations so that they attain a mutually right-and-left paired relation at a front side and a rear side of the walking direction based on the lumbar region, and
wherein the control unit is configured to independently drive each of the first tension adjusting parts and each of the second tension adjusting parts.

4. The walking aid device according to claim 1, further comprising:
a treadmill which is mounted integrally with the drive part, and moves a walking belt in a circular motion according to a rotation of rollers.

5. The walking aid device according to claim 4, further comprising:
adjustment mechanism parts which support four corners of the treadmill in a state where the walking belt can be moved in a circular motion, and in which height adjustment can be independently performed in each of the supported four corners,
wherein, by adjusting the supported four corners in a pair relation of either a front side or a rear side or a pair relation of either a left side or a right side relative to a treadmill's advancing direction among a plurality of the support locations by a predetermined height, the adjustment mechanism parts causes the walking surface of the walking belt to incline relative to a floor surface at an angle according to the predetermined height around a pitch axis or a roll axis.

6. The walking aid device according to claim 5,
wherein the adjustment mechanism parts have an actuator and a lifting mechanism at each of the treadmill's four corners, and the lifting mechanism lifts and moves the support locations according to a drive of the actuator, and
wherein, when an angle of inclination around a pitch axis or a roll axis on a walking surface of the walking belt is externally input, the control unit is configured to drive each of the corresponding actuators so that each of the support locations become a height position corresponding to the angle of inclination.

7. The walking aid device according to claim 1,
wherein wheels are each mounted on a ground end of the frame supporting the drive part, the gait recognition unit and the control unit, and
wherein the drive part moves integrally with the user according to a walking motion of the user in a supported state.

8. The walking aid device according to claim 7,
wherein the drive part further comprises a wheel drive part which engages with at least a pair of left and right wheels among a plurality of the wheels, and which is capable of independently driving each of the wheels according to control of the control unit, and
wherein the control unit is configured to control the wheel drive part so as to adjust a driving speed and a rotating direction of each of the wheels to match the user's walking motion based on the recognition result of the gait recognition unit.

* * * * *